United States Patent [19]

Brodie et al.

[11] Patent Number: 5,980,620

[45] Date of Patent: Nov. 9, 1999

[54] INHIBITION OF BACTERIAL GROWTH

[76] Inventors: Harold Brodie, Highfield, Histons Hill, Codsall, Staffordshire WV8 2ER; Rainer Clover, 418a Sutton Road, Walsall, West Midlands WS5 3BA, both of United Kingdom

[21] Appl. No.: 09/201,287

[22] Filed: Nov. 30, 1998

Related U.S. Application Data

[63] Continuation of application No. PCT/GB96/01374, Jun. 5, 1996, abandoned.

[51] Int. Cl.$^6$ .............................. A01N 25/12; A01N 25/10
[52] U.S. Cl. ................................... 106/15.05; 106/18.32; 106/18.35; 424/405; 424/409; 424/419; 523/122; 514/360; 514/398; 514/588; 514/596; 514/721
[58] Field of Search ........................... 106/15.05, 18.32, 106/18.35; 523/122; 424/405, 409, 419; 514/360, 398, 588, 596

[56] References Cited

U.S. PATENT DOCUMENTS

| | | | |
|---|---|---|---|
| 3,817,761 | 6/1974 | Brake | 106/15 |
| 3,817,762 | 6/1974 | Brake | 106/15 |
| 3,988,294 | 10/1976 | Hill | 260/45.8 |
| 4,629,645 | 12/1986 | Inoue | 428/141 |
| 4,663,364 | 5/1987 | Iwasaki et al. | 523/122 |
| 4,851,421 | 7/1989 | Iwasaki et al. | 514/352 |
| 5,053,444 | 10/1991 | Trotoir | 523/351 |
| 5,238,749 | 8/1993 | Cueman et al. | 428/441 |

FOREIGN PATENT DOCUMENTS

| | | |
|---|---|---|
| 2409250 | 6/1979 | France . |
| 2657085 | 7/1991 | France . |
| WO 91/08268 | 6/1991 | WIPO . |

OTHER PUBLICATIONS

Japanese Patent Abstract No. JP408060036A, abstract of Japanese Patent Specification No. 08–060036, Mar. 1996.
WPIDS Abstract No. 94–072114, abstract of Japanese Patent Specification No. 06–025561, Feb. 1994.
WPIDS Abstract No. 94–106899, abstract of Japanese Patent Specification No. 06–057032, Mar. 1994.
Patent Abstract of Japan, vol. 96, No. 7 & JP 08060036 (see Abstract) (Mar. 1996).
Database WPI, Section Ch, Week 9409, Derwent Publications, Ltd., AN 94–072114, XP002024460 & JP 06025561 (see Abstract) Feb. 1994.
Database WPI, Section Ch, Week 9413, Derwent Publications, Ltd., AN94–106899, XP002024461 & JP 06057032 (See abstract) Mar. 1994).

*Primary Examiner*—Anthony Green
*Attorney, Agent, or Firm*—Caesar, Rivise, Bernstein, Cohen & Pokotilow, Ltd.

[57] ABSTRACT

The invention provides a means of inhibiting bacterial growth particularly on a coated substrate. It comprises a method of forming a substantially dry powder coating containing a biocide, applying the powder coating composition to form a coating on the substrate, the biocide being capable of retaining effective biocidal activity in the coating.

11 Claims, No Drawings

INHIBITION OF BACTERIAL GROWTH

This application is a continuation of PCT/GB96/01374 filed Jun. 5, 1996 and is now abandoned.

This invention relates to the inhibition of bacterial growth and particularly to the inhibition of bacterial growth on a substrate. It is an object of the invention to provide an anti-bacterial coating composition to be applied to a substrate.

In one aspect the invention provides a substantially dry powder coating composition comprising particles each of which is a polymer powder and contains biocide, whereby the biocide is substantially uniformly distributed throughout the composition.

In another aspect the invention provides an article having an anti-microbial coating thereon, the coating comprising a matrix of set polymer and containing particles of biocide therein, the biocide particles being substantially uniformly distributed throughout the coating.

In a third aspect the invention provides a method of distributing a biocide substantially uniformly in a powder coating composition, the method comprising:

mixing precursors of a polymer powder and of a biocide and heating the mixture;

extruding the hot mixture into sheet form;

granulating the sheet;

grinding the granules to powder, and sieving the powder to size.

Particularly suitable polymer powders to form the matrix of the coating composition include thermosetting polymers such as epoxy, polyesters, and epoxy-polyesters, acrylics and polyurethanes. The precursors are the resin and the hardener therefor these are available in powder form, pre-pigmented and clear. They may be used to provide a variety of desired surface finishes—gloss, matt and textured. The invention is also applicable to other polymeric powder materials, e.g. thermoplastic materials, e.g. nylon, polyethylene, polypropylene and eva and pva.

Typically the powders have a specific gravity of from 1.2 to 1.9 and a particle size of which 100% is less than 100 microns and 40 to 60% is greater than 34 microns. The thermosetting powders may have stoving temperatures, for example, of at least 120°, e.g. 140° to 210° C. depending, of course, as the physical characteristics of the specific material used. They may also be cured by ultraviolet light or like processes.

The selected biocide may be active against Gram positive and/or Gram negative bacteria, algae, filamentous fungi or yeasts and may be a general purpose biocide that is active against more than one such category. Many biocides may be suitably employed in the invention and the average skilled man of the art will readily be able to determine by routine experimentation whether the biocidal activity of any particular biocide will be sufficiently retained for his particular needs in the coating. The necessary criteria are that the biocide can be provided in a suitable powder form and that it can survive the coating process.

Particularly suitable classes of biocides have been found to include:

trichlorohydroxydiphenyl ethers, e.g. 2,4,4'-trichloro-2'-hydroxydiphenylether, methylureas, e.g. 3.-(3,4-dichlorophenyl)-1,1-dimethylurea, imidazolcarbamates.

The amount of biocide incorporated in the powder composition will vary depending on the intended end use and the strength and nature of the particular biocide. Thus suitable amounts can readily be determined from the known mic values of the particular biocide. For example, up to 20% by weight of biocide based on the total powder composition may be used. Typically useful proportions are from 0.1 to 10% by weight of the total powder composition, especially from 2 to 6% by weight.

Other ingredients may be included in the powder composition, for example pigments, fillers, fluidity agents, dispersants, preservatives; and the like.

The matrix powder incorporating the biocide powder has good shelf life depending on the particular biocide used but, alternatively, may be manufactured shortly prior to use.

The article to which the coating is applied is preferably metal, although the invention is not limited thereto and includes any substrate capable of being powder coated, for example, domestic appliances (so-called white and brown goods), work surfaces for domestic and industrial use, architectural and other engineering products, such as hand rails, door handles and plates; garden furniture; and the like. Typical substrates may be, for example, ferrous metals, zinc-coated steels, aluminium, wood and the like. The article may thus be used in any environment where hygiene is advantageous.

The powdered coating compositions of the invention may be applied by electrostatic spraying which may be manual or automatic, or by tribocharged spraying, plastics coating (fluidised bed); or the like.

The biocide may be incorporated in the powder which forms the matrix of the coating. As each particulate contains the biocide it is homogeneously distributed throughout the coating composition and so cannot separate out. Thus, for example, such a powder may be made by adding the biocide at the initial mixing stage of the constituents which are to be converted into the desired matrix powder. In a typical powder manufacturing process, the precursors of the desired powder, e.g. the resin base and its hardener, together with the biocide and any other additives such as pigments, fillers, are mixed, heated and extruded to sheet form, the sheet is granulated and then ground and sieved to the desired powder size. Excellent mixing of the constituents is thereby achieved and all the constituents in the desired proportions are present in each of the individual particles of the final powder.

As is well appreciated in the coating art, the substrate must be thoroughly clean before application of the powder mixture and cleaning, e.g. by shot-blasting and/or chemical means may be carried out by conventional means.

Specific embodiments of the invention are further described in the following Examples:

EXAMPLE 1

Pigmented powdered coating compositions were made by mixing the following powder materials in the proportions shown

|  | Parts by weight |
| --- | --- |
| BIOCIDE | 0 to 6 |
| Matrix powder | 100 to 94 |

The BIOCIDE was a 2,4,4'-trichloro-2'hydroxy diphenylether supplied by CIBA GEIGY as IRGASAN DP 300. The matrix powder was a proprietary polyester powder.

The powdered mixture was sprayed electrostatically onto one metal surface which had previously been degreased shot-blasted to provide several sample slides coated on one surface only.

Bacterial lawn plates of five different bacteria, as listed in Table 1 below, in Tryptone Soya Agar were prepared and a sample slide was placed, coated side down, in the centre of each plate. The plates were incubated at 37° C. for 24–48 hours and observed for zones of inhibition.

The results are listed in Table 1 below, being based on 3 replicates per slide:

TABLE 1

| | Percentage of Biocide | | | |
|---|---|---|---|---|
| Organism | 0 | 2 | 4 | 6 |
| E. Coli | --- | +-- | +-- | +-- |
| P. aeruginosa | --- | +-- | +-- | +-- |
| S. typhimurium | --- | --- | --- | --- |
| S. aureus | +-- | +-- | +-- | +-- |
| S. faecalis | --- | --- | +-- | --- |

EXAMPLE 2

A powdered coating composition was made by mixing the following powder materials in the proportions shown.

| | Parts by weight |
|---|---|
| BIOCIDE | 6 |
| Matrix powder | 94 |

The BIOCIDE was as in Example 1.

The matrix powder was a polyester supplied by H B Fuller Coatings Limited, Birmingham, England under the identification OMEGA PC P6/035.

The powder mixture was sprayed on to microscope glass slides of about 25 mm width at a temperature of 200° C. for five minutes.

Bacterial lawn plates of eight different bacteria, as listed in Table 2 below, were prepared as follows. The coated slides were placed, coated face upwards in Petri dishes containing Agar nutrient as for Example 1. A thin film of the nutrient covered the test slides. Each bacteria was applied in a line across a dish and continuing over the test slide. As before, a set of three samples were tested in each instance, i.e. in each Run.

In Table 2 are listed the Degree of Inhibition (DOI) and the Zone of Inhibition (ZOI) in mm. The DOI indicates the amount of the width of each line of bacteria that disappeared and the DOI indicates the amount of the length of the line of organisms across and on either side of its slide that disappeared.

| | Run 1 | | Run 2 | |
|---|---|---|---|---|
| Organism | DOI | ZOI (mm) | DOI | ZOI (mm) |
| Staphylococcus aureas (Oxford) | Complete | 55 | Complete | 55 |
| Staphylococcus aureas (Resistant) | Complete | 50 | Complete | 45 |
| Enterococcus faecalis | 50% | 25 | 50% | 25 |
| Escherichia-coli | Complete | 30 | Complete | 30 |
| Salmonella typhimurium | Complete | 30 | Complete | 30 |
| Pseudomonas aeruginosa | NIL | — | NIL | — |
| Corynebacterium diptheria (non-toxic) | 50% | 25 | 50% | 25 |
| Bacillus subtilis | Complete | 35 | Complete | 35 |

EXAMPLE 3

Example 2 was repeated but using the six organisms listed in Table 3 below and using biocide concentrations of from 0 to 20% by weight. The Zones of Inhibition were again measured and are listed in Table 3.

TABLE 3

| | Biocide concentration (% w/w) | | | | |
|---|---|---|---|---|---|
| Organism | 0 | 6 | 10 | 15 | 20 |
| E. coli | 0 | 31 | 43.7 | 57.3 | 49.3 |
| Strep faecalis | 0 | 25 | 25 | 25 | 26.7 |
| S. aureas (Oxford) | 42 | 52.3 | 76.7 | 100 | 100 |
| S. aureas (Resistant) | 42.3 | 53.7 | 100 | 100 | 100 |
| P. aeruginosa | 0 | 0 | 0 | 0 | 0 |
| B. subtilis | 0 | 26 | 32 | 41.6 | 43 |
| Salmonella typhimurium | 0 | 25.3 | 32 | 39 | 43 |

EXAMPLE 4

Compositions (see Table 4) were made up of different plastics using the respective uncured resin and hardener systems, 5% by weight of the biocide added and the mixture then heated. The hot mixture was extruded into sheet form, granulated and then ground, followed by sieving to an average particle size below about 100 micron. On analysis it was noted that substantially each plastics powder particle contained a particle of the biocide. The powders were powder sprayed on to test panels, stoved or u.v. cured in the case of thermoset powders, and then tested for microbiological activity according to the known modified 147 test using 15 mm discs. The results obtained are shown in Table 4.

It will be appreciated that the invention is not limited to the specific embodiments described. For example, another suitable technique for applying the coating to a metal substrate is the so-called plastics coating technique in which the substrate is preheated and dipped into a bed of the powder. Such a technique also forms part of this invention.

TABLE 4

| Biocide Triclosan | Plastics Clear EP | *Listeria Monocytogenes* | *Escherichia Coli* | *Staphylococcus Aureus* | *Staphylococcus aureus* (Res) | *Bacillus Subtilis* | *Streptococcus Faecalis* | *Salmonella Typhimurium* |
|---|---|---|---|---|---|---|---|---|
| 0 | Clear EP | 0 | 0 | 19 | 17 | 0 | 0 | 0 |
| Triclosan | Clear EP | 16 | 17 | 25 | 23 | 17 | 16 | 17 |
| 0 | Pigmented EP | 0 | 0 | 0 | 0 | 0 | 0 | 0 |
| Triclosan | Pigmented EP | 17 | 23 | 39 | 39 | 21 | 16 | 23 |
| 0 | Pigmented EP | 0 | 0 | 0 | 0 | 0 | 0 | 0 |
| Triclosan | Pigmented EP | 0 | 19 | 25 | 25 | 25 | 0 | 15 |
| Triclosan | Pigmented EP | 0 | 19 | 29 | 29 | 29 | 0 | 17 |
| 0 | Clear polyester | 0 | 0 | 0 | 0 | 0 | 0 | 0 |
| Triclosan | Clear polyester | 19 | 17 | 25 | 15 | 19 | 16 | 19 |

EP = epoxypolyester
Triclosan = 2,4,4$^1$-trichloro-2$^1$-hydroxydiphenylether

We claim:

1. A substantially dry powder coating composition comprising particles each of which is a thermosetting polymer powder and contains an organic biocide, in a concentration of from 0.1 to 20% by weight, the composition being in the form of particulates each comprising the polymer powder containing the biocide, whereby the biocide is substantially uniformly distributed throughout the composition.

2. A powder coating composition according to claim 1, wherein the biocide is present in an amount of from 2 to 6% by weight.

3. A powder coating composition according to claim 1, wherein the biocide is a trichlorohydroxydiphenylether.

4. A powder coating composition according to claim 3, wherein the biocide is 2,4,4'-trichloro-2'-hydroxy diphenylether.

5. A powder coating composition according to claim 1, wherein the biocide is a methylurea.

6. A powder coating composition to claim 5, wherein the biocide is 3-(3,4-dichlorophenyl)-1,1-dimethylurea.

7. A powder coating composition according to claim 1, wherein the biocide is an imidazolcarbamate.

8. A powder coating composition according to claim 1, wherein the polymer powder has a specific gravity of from 1.2 to 1.9 and a particle size less than 100 microns.

9. A powder coating composition according to claim 1, wherein the polymer particles comprise a polyester or epoxypolyester or polyurethane or acrylic or other thermosetting powder.

10. A method of distributing an organic biocide substantially uniformly in a thermosetting powder coating composition, the method comprising:
    mixing precursors of the thermosetting polymer powder together with the organic biocide in a concentration of 0.1 to 20% by weight and heating the mixture to form a hot mixture:
    extruding the hot mixture into sheet form;
    grinding the granules to a powder having the size of particles appropriate to powder coating; and
    sieving the powder to less than 100 microns whereby the powder may be sprayed electrostatically.

11. A method of forming a coating on a metal substrate wherein said coating exhibits anti-microbial activity, the method comprising:
    mixing precursors of a thermosetting polymer powder together with particles of an organic biocide to form a mixture and then heating the mixture;
    extruding the hot mixture into sheet form;
    granulating the sheet to form granules;
    grinding the granules to form a powder;
    sieving the powder to the size of particles appropriate to electrostatic spraying;
    electrostatically spraying the sieved powder on to the metal substrate to form said coating and;
    curing the coating to provide said anti-microbial coating on the metal substrate.

* * * * *